US011322049B2

(12) United States Patent
Lint et al.

(10) Patent No.: US 11,322,049 B2
(45) Date of Patent: May 3, 2022

(54) AUTOMATED EXTERNAL DEFIBRILLATOR TRAINING DEVICE WITH MANUAL INPUT AND AUDIO OUTPUT CONTROLS FOR PROGRAMMING

(71) Applicant: PRESTAN PRODUCTS LLC, Mayfield Village, OH (US)

(72) Inventors: Timothy E. Lint, North Royalton, OH (US); John J. Pastrick, University Heights, OH (US)

(73) Assignee: PRESTAN PRODUCTS LLC, Mayfield Village, OH (US)

( * ) Notice: Subject to any disclaimer, the term of this patent is extended or adjusted under 35 U.S.C. 154(b) by 665 days.

(21) Appl. No.: 16/014,783

(22) Filed: Jun. 21, 2018

(65) Prior Publication Data

US 2018/0374391 A1 Dec. 27, 2018

Related U.S. Application Data

(60) Provisional application No. 62/523,051, filed on Jun. 21, 2017.

(51) Int. Cl.
*G09B 23/00* (2006.01)
*G09B 23/28* (2006.01)
*A61N 1/39* (2006.01)
*G09B 19/00* (2006.01)

(52) U.S. Cl.
CPC ......... *G09B 23/288* (2013.01); *A61N 1/3993* (2013.01); *G09B 19/00* (2013.01)

(58) Field of Classification Search
None
See application file for complete search history.

(56) References Cited

U.S. PATENT DOCUMENTS

| 4,588,383 A * | 5/1986 | Parker .................. G09B 23/288 434/265 |
| 2003/0036044 A1* | 2/2003 | Pastrick ............... G09B 23/288 434/265 |
| 2010/0198375 A1 | 8/2010 | Rottler |
| 2017/0076634 A1* | 3/2017 | Hoss ...................... G09B 23/30 |

* cited by examiner

*Primary Examiner* — James B Hull
(74) *Attorney, Agent, or Firm* — Ulmer & Berne LLP

(57) ABSTRACT

An electronic AED training device with a user programming system which uses manual input controls and audio output programming controls for programming the desired features of the AED training device. The audio output programming controls comprise an audio-based output menu providing voice prompts describing the features of the menu item. The manual input controls include manual buttons in electronic communication with the user programming system. One manual button operates selection of a menu item within the programming system and a second manual button selects a training option available within the menu item.

6 Claims, 5 Drawing Sheets

FIGURE 3A ( SETUP MODE )

11

UPON MB FROM OFF STATE OR
UPON MB FROM ANY TRAINING STATE

Setup Mode
PB LED = On
Enable ChgB, ONLY in this state

"SCENARIO #" (Current #)

If ChgB next, prompts and changes to next Shock Scenario # option.
Repeat for each ChgB until MB pressed.

Next MB prompts current Shock Type
"SEMI-AUTOMATIC" or "AUTOMATIC"

If ChgB next, prompts and changes to next Shock Type option.
"SEMI-AUTOMATIC" or "AUTOMATIC"
Repeat for each ChgB until MB pressed again.

Next MB prompts current Ventilations setting
"VENTILATIONS ON" or VENTILATIONS OFF"
If ChgB next, prompts and changes to next Ventilations setting.
And so on per below Menu..

Settings Menu — 40   42   42   42   42   42

| Name | Option 1 (Default) | Option 2 | Option 3 | Option 4 | Option 5 |
|---|---|---|---|---|---|
| 1) Shock Scenario | "SCENARIO 1... S S S" | "SCENARIO 2... S NS NS" | "SCENARIO 3... NS NS NS" | "SCENARIO 4... S NS S" | "SCENARIO 5... S S NS" |
| 2) Shock Type | "SEMI-AUTOMATIC SHOCK" | "AUTOMATIC SHOCK" | | | |
| 3) Ventilations | "VENTILATIONS ON" | "VENTILATIONS OFF" | | | |
| 4) Metronome | "CPR METRONOME ON" | "CPR METRONOME OFF" | | | |

TO FIGURE 3B

FROM FIGURE 3A

Menu Button (MB) Function:
The current Scenario # is always prompted first upon entry into Setup.
MB selections then increment through the menu and prompt each of the current settings.
Each successive MB selection will each prompt the next setting in the Menu order as shown.
MB selections will always interrupt any prompt (MB or CngB) and immediately advance
to prompt the next Menu setting.
The menu is circular and returns to the first setting after prompting the last.

Change Button (ChgB) Function:
Increments through the available options for any particular Setting.
The ChgB simply advances to the next option for the setting last prompted and prompts the name of
the new option and places in RAM.
Options increment left to right as listed in Menu.
ChgB will also interrupt any prompt (MB or ChgB) and immediately advance to prompt the next option.
The option menus are circular and return to the first option after prompting the last.

Start 2 Second Timer after last prompt played on a given menu line.
If Setup Timer = 0, Exit immediate
If VB Pressed, Exit immediate to Volume Mode
If LB Pressed, Exit immediate to Language Mode
Upon PB Press Exit Immediate.

Upon Exit:Place all new selections in RAM so EE Write will detect changes.
PB LED = Off
---
Accept: LB, VB, MB, ChgB, PB
Ignore SB, CB Upon T=0,
Upon PB Press

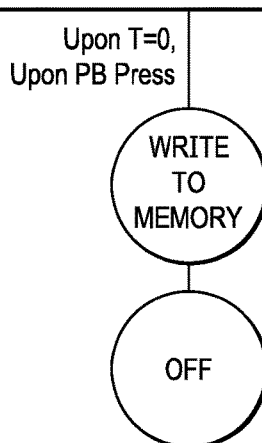

FIGURE 3B

AUTOMATED EXTERNAL DEFIBRILLATOR TRAINING DEVICE WITH MANUAL INPUT AND AUDIO OUTPUT CONTROLS FOR PROGRAMMING

CROSS-REFERENCE TO RELATED APPLICATIONS

This application claims priority from U.S. Provisional Application Ser. No. 62/523,051 filed Jun. 21, 2017, which is incorporated herein by reference.

FIELD

The present application relates generally to electronic devices, and more particularly, to an automated external defibrillator training device using a system and method for user programming having audio output controls and minimal manual input controls.

BACKGROUND

An automated external defibrillator (AED) is an electronic device that diagnoses life-threatening cardiac arrhythmias of ventricular fibrillation and ventricular tachycardia in a patient. Once diagnosed, the AED device attempts to treat the condition through defibrillation, which is the application of electrical therapy to stop the arrhythmia, and allow the heart to reestablish an effective rhythm.

The operation of an AED device preferably involves considerable and repeated training prior to use on a patient. In order to supply prior training on the proper use of an AED device, less expensive AED training devices or AED trainers, which are incapable of providing any actual diagnostics treatment or any electrical therapy, have been developed to provide both professional health care providers and the general public with appropriate AED training.

Using simple audio output and visual output commands, AED's are designed to be easy to use for the layperson. The use of AED's is taught using AED training devices in many first aid, certified first responder, and basic life support level cardiopulmonary resuscitation (CPR) classes. Since the use of AED training devices has become common in first aid training classes, the simple and efficient programming of the desired settings or training features in the AED training devices is also desirable for the first aid teachers and trainers using the devices during their classes. While expensive AED training devices are available for purchase, limited funds for low budget first aid training classes makes the use of such expensive AED training devices prohibitive. As a result, there is a need for low cost AED training devices that are easy and efficient to program for first aid teachers, but that also communicate well the proper use of the AED devices to their students.

Prior art electronic devices such as an AED training devices have used visual systems to communicate output commands for ease of programming training features of the devices. Such AED training devices may have included liquid crystal displays (LCD) for communicating output instructions using words, symbols or numbers displayed on the LCD screen, as well as light emitting diode (LED) displays, with white and colored lights, indicating, for example, device conditions, or success or failure in both programming and use of the AED training device.

SUMMARY OF THE INVENTION

The present AED training device uses manual input controls and audio output controls for device programming, but does not include an LCD or other visual output controls for device programming. The programming controls, or programming system, for the electronic device comprise an audio-based menu system with a manual button input control system which has only one, only two or only three manual control buttons. The preferred AED training device includes an audio-based output menu system and two manual input control buttons, where one manual input control button is a menu button and a second manual input control button is a change button.

In the present electronic AED training device, to program the setup of the AED training device, the menu button is pressed (or manually operated) by the individual operating the AED training device. While every manual button operation yields a corresponding audio output prompt, the menu button operation is specifically used to enter the AED training device setup mode and to advance through the training feature options.

Upon selecting or operating the menu button, the AED training device is powered on (when entered from a power off position) and setup mode is entered. Likewise, selecting the menu button when the AED training device is already powered on and in a training mode, enters the setup mode, such that resuming in the training mode requires restarting training.

The AED training device may be programmed to train a student using the AED training device in a variety of training feature formats. After pressing the menu button, the current training option for the first menu item is played, meaning a voice prompt of the first menu item is heard from the audio output controls. If no further selections are made, the AED training device turns itself off. To hear additional training options, the menu button may be pressed to scroll, move or advance through the training feature options for each menu item. After each successive operation of the menu button, the next training option is provided by the audio output system so that the trainer or teacher may sequentially hear the currently selected training options for each menu item. By repeatedly pressing the menu button and listening to the currently programmed training options, the trainer or teacher may review or move through the entire menu. If the trainer wishes to change an option, they simply press the menu button until they hear the training option they wish to change. To change to a different option for the menu item, the second manual input control button, the change button, is pressed to select and play the next training option for that particular menu item. The trainer can repeatedly press the change button until the desired training option for that menu item is played and thereby selected. For example, upon hearing the audio output indicating the current training option for a preset emergency scenario, the trainer or teacher may desire to select a different preset or preprogrammed emergency scenario training option by pressing the change button. Once within the desired level or menu item option of the programming control system, the individual preset/ programmed emergency scenarios may be heard by repeatedly pressing the change button to hear or play output descriptions of the multiple available preset/preprogrammed emergency scenario options for handling by the student using the AED training device. Once the desired output training scenario is heard, no further pressing of the change button is necessary. The last training option heard is then the selected or current programmed training option. The device times out or powers off after a desired time (for example, as few as 2 or as many as 5 or more seconds) to save the last item heard or played. The programming control system programs a menu item selection when the trainer or teacher stops pressing the change button, assuming that the last item heard or played is the desired menu item option and saves this selection.

Using the technique of moving through multiple levels of available programming training feature options by operating the menu button, and entering the desired programming level to be changed by operating the change button until the desired training option is heard, the present electronic training device eliminates the use of an expensive LCD or LED output display system. The programming control system takes advantage of the conventional speaker already included in the audio training device, instead of additionally requiring visual outputs for programming. The present device enables electronic setup programming using an audio output control system and a manual button input control system as programming controls.

DRAWING DESCRIPTIONS

FIGS. 3A and 3B, which may be referred to collectively as FIG. 3, are a partial enlarged schematic flow chart showing the setup programming mode of the AED training device, and specifically the training menu and options within the setup programming mode.

Figure 1:
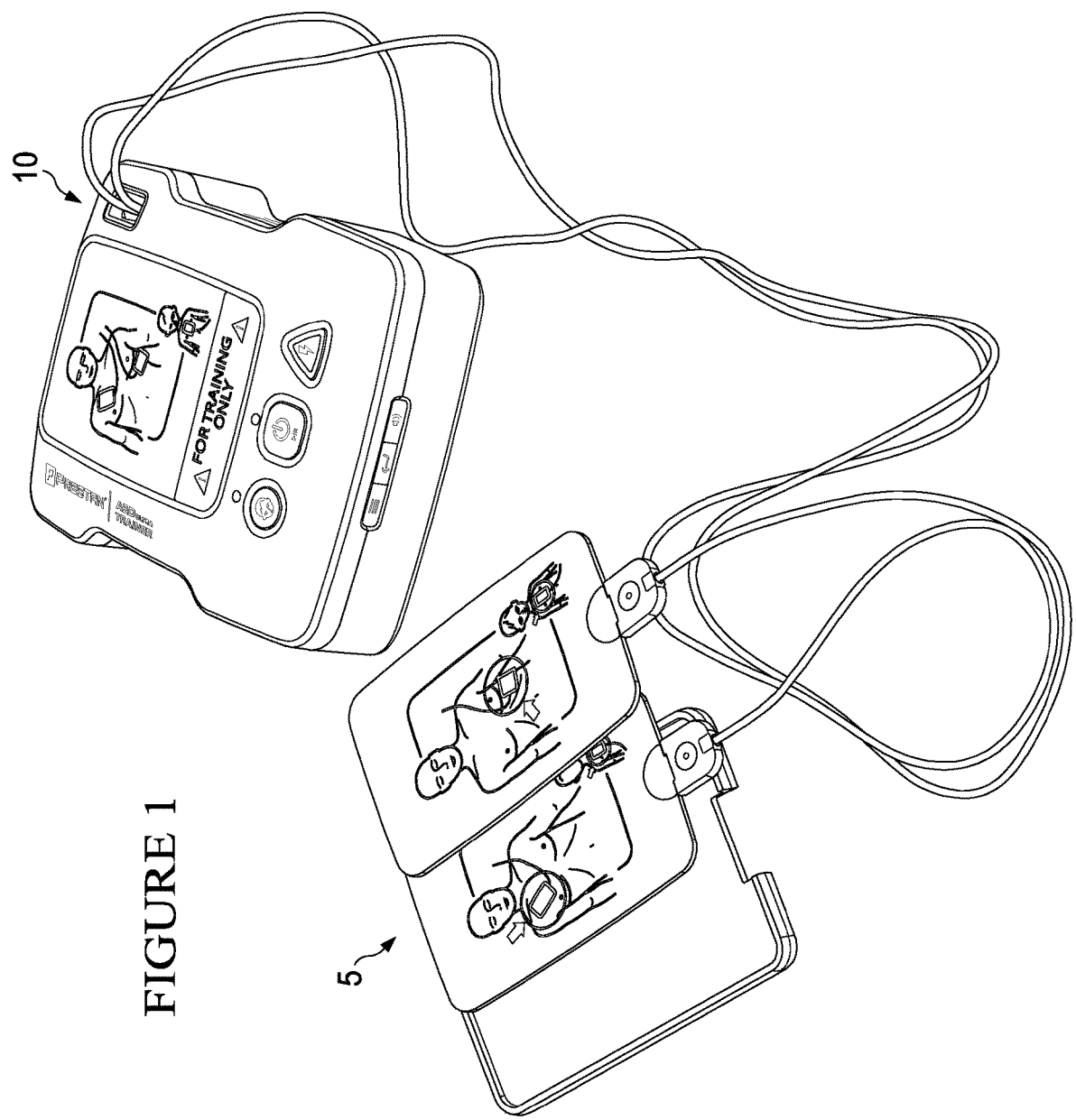
FIG. 1 shows a perspective view of an electronic AED training device with connected training pads having the programming system of this application.
Figure 4:
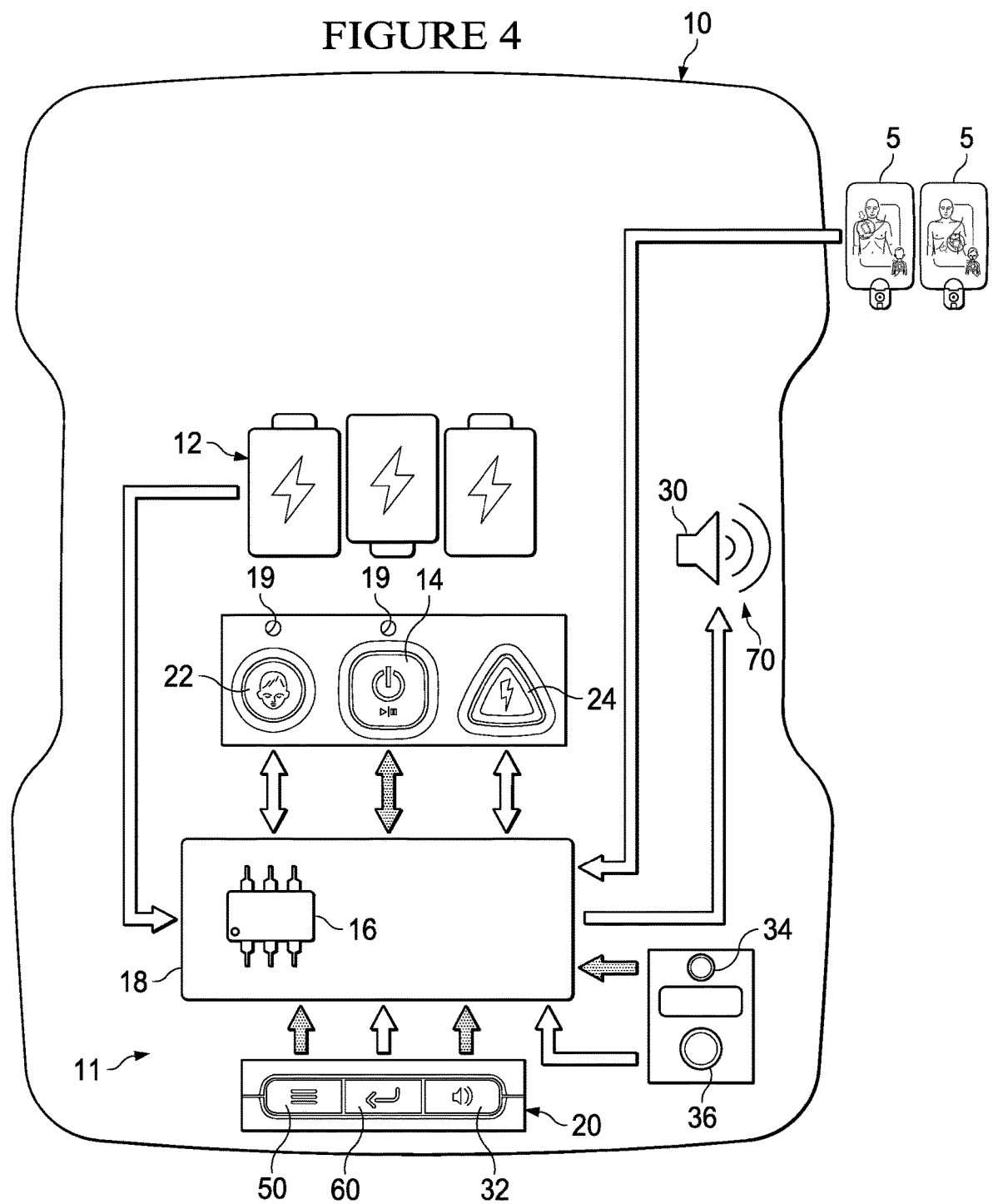

FIG. 4 is a schematic illustration showing the control system and related input and output components of the electronic AED training device of FIG. 1.

DETAILED DESCRIPTION

Figure 2:
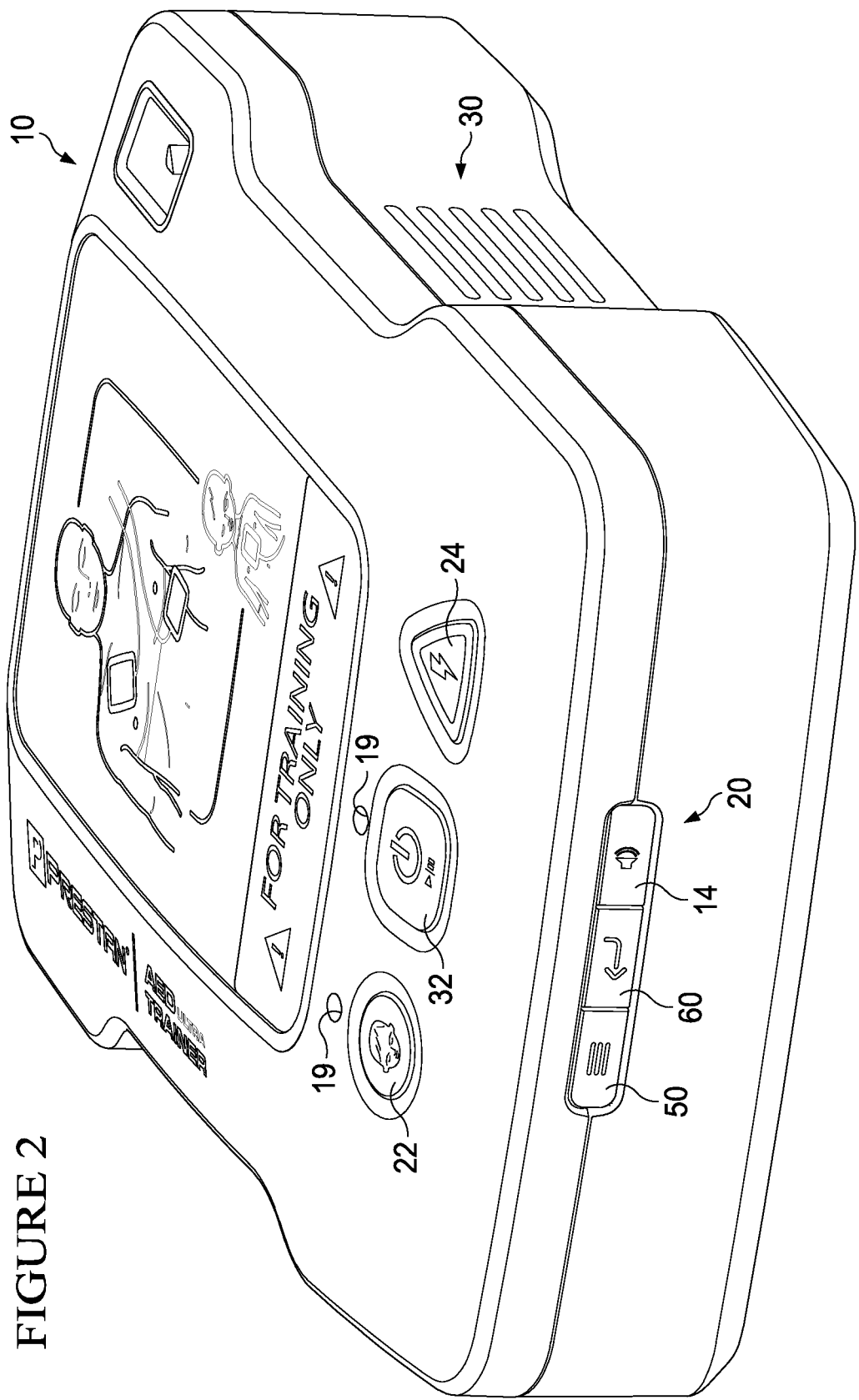
FIG. 2 shows a perspective end view of the electronic AED training device of FIG. 1, showing the power button and LED lights on a top surface of the device, and the menu, change and volume buttons on the end surface of the device (at the left, middle and right positions, respectively).

The present application provides an electronic device, specifically an electronic AED training device 10 having a programming system, FIGS. 1 and 2, which is programmed using manual input 50, 60 and audio output 70 programming controls. The programming system 11 allows a user to configure the AED training device 10 for the desired training features, such as defibrillation training pattern scenarios. The system and method for programming includes control system 18 having an audio-based output menu system 70 and manual input controls in the form of a manual button system 20, which has one, two or three push button controls. In the preferred embodiment illustrated, the manual button system 20 has two manual input control buttons: a menu button 50 and a change button 60. However, it should be understood that a single manual input control button would likewise enable operation of the system, where the function to change the training feature selection is enabled by a double click or two rapid successive pressings of the one input control button by the device operator, teacher or programmer. For example, in a one button embodiment, the output indicators comprise audibly playing recorded audio descriptions of multiple available training feature options, and the manual input control comprises a manual button in electronic communication with the setup programming system. One operation of the manual button would operate to select a training feature option within the setup programming system and two rapid successive operations of the manual button would select an option from the menu.

In addition to the manual input button system 20 and audio output system 70 described in the present two button embodiment, the electronic AED training device 10 includes a power supply 12 interconnected with a power button 14, shown in FIGS. 1, 2 and 4, and an electronic memory 16 where desired training feature options are saved and read, all using an electronic control system 18, as in FIG. 4. The electronic device 10, control system and programming system 11 of the preferred embodiment, include for example, conventional tactile switch buttons 50, 60, conventional audible speech output via a speaker 30, external memory 16 to store pre-recorded speech (audio output), all of which is controlled by the control system 18, using a 16-bit microcontroller, which is programmed by the manufacturer using a Windows® executable program which enables program code to be downloaded to the microcontroller via the USB port 36. Interconnected LED output indicator lights 19, are also provided, as shown in FIGS. 1 and 4, to indicate when the device 10, or a feature of the device, such as activation of the child mode using the child button 22, is in use. The power button 14 operates to power the AED training device 10 on and off, and also provides a pause feature. When the AED training device 10 is in the on mode or state, the associated LED output indicator light 19 is illuminated in green. As shown in FIG. 4, solid black input and output arrows are used to indicate that these buttons 14, 50, 60 also operate to power or wake up the AED training device 10 on from the power off mode or paused state. Use of the illuminated shock button 24 by the user is pursuant to instructions during training. Training pads 5 are electrically interconnected with the device 10 to confirm proper use during training.

For a user, such as a teacher, to begin selecting specific programming features for use in training with the electronic device 10 of FIG. 1, the menu button 14 is operated to power on the device from an off state and to enter the setup mode, where programming of the device operation is controlled.

It should be understood that the orientation of the programming levels or training feature options of the present electronic AED training device are arranged such that the menu items available can be depicted in a row and column matrix structure. In the embodiment of this application, the training feature menu items 40 are presented on a vertical axis. Within, under or associated with each menu item 40 are alternative training feature options 42, which are depicted on a horizontal axis as shown in FIG. 3, and which are audibly heard by the user as they are played over the audio output system 70 and speaker 30 used by the audio enabled AED training device 10 A sample of the audio setup menu structure from FIG. 3 is set forth in Table 1, where in the desired sequence of AED training device training feature options to be programmed, S equals Shock, and NS equals No Shock:

TABLE 1

| Menu Items | Available Options (in the form of Audio Prompts) | | | | |
|---|---|---|---|---|---|
| | Option 1 (Default) | Option 2 | Option 3 | Option 4 | Option 5 |
| Shock Scenario | Shock Scenario 1: S S S | Shock Scenario 2: S NS NS | Shock Scenario 3: NS NS NS | Shock Scenario 4: S NS S | Shock Scenario 5: S S NS |
| Shock Type | Semi-Automatic Shock | Automatic Shock | | | |
| Ventilations | Ventilations On | Ventilations Off | | | |
| Metronome | CPR Metronome On | CPR Metronome Off | | | |

As shown in FIG. 3, the abbreviations below have the following meanings: PB=power button; ChgB=change button; MB=menu button; VB=volume button; LB=language button; CB=child mode button; SB=shock button; and items indicated between quotation marks are audio prompts or aural instructions emitted from the AED training device speakers (e.g., "Shock" means that the word "shock" is audibly emitted 70 from the AED training device output speaker 30 for hearing by the user).

Once the menu button 50 is selected and repeatedly pressed, the audio output system 30, 70 is used to move, scroll or advance through all of the vertically depicted menu items 40 available, and the current programmed training feature options of the device for each menu item are audibly played by the system output speaker 30, 70. By continually pressing the menu button 50, the audio output system 30, 70 continues in a loop or circular fashion to play repeatedly each of the currently programmed or selected training feature options. When a different training option 42 is desired than the option audibly played, the change button 60 can be pressed to play and hear the alternative training feature options 42. By continually pressing the change button 60, the audio output system 30, 70 continues in a loop fashion to audibly play repeatedly each of the available training options 42 within the menu item 40. When the desired training option 42 is played, no further operation of the change button 60 is required, and after a few seconds, the programming control system 18 will time out and save the last training option played to memory 16 as the new programmed training feature, and turns off the AED training device 10 automatically.

Alternatively, the available training feature menu items may be arranged as either rows or as columns. As shown in the "Settings Menu" in the flowchart of FIG. 3, and Table 1, the training feature menu items 40 are on the vertical axis or first column, and the training feature options 42 are positioned horizontally. The below Table 2 menu arrangement provides an equivalent settings menu to Table 1, but reversed, where the menu items 40 are along the horizontal axis or first row, and the training option items 42 are positioned vertically, and in the desired sequence of AED training device operations to be programmed, S equals Shock, and NS equals No Shock:

TABLE 2

| Available Options | Menu Items | | | |
|---|---|---|---|---|
| | Shock Scenario | Shock Type | Ventilations | Metronome |
| Option 1 (Default) | Shock Scenario 1: S S S | Semi-Automatic Shock | Ventilations On | CPR Metronome On |
| Option 2 | Shock Scenario 2: S NS NS | Automatic Shock | Ventilations Off | CPR Metronome Off |
| Option 3 | Shock Scenario 3: NS NS NS | | | |
| Option 4 | Shock Scenario 4: S NS S | | | |
| Option 5 | Shock Scenario 5: S S NS | | | |

A vertical menu orientation as schematically shown in the flow chart of FIG. 3, and Table 1, under "Settings Menu," is provided in the present embodiment, where four (4) settings are depicted as available menu item 40 options. However, it should be understood that any number of desired menu items 40 and training options 42 may be included, as later features or options may be desired and added. The illustrated sample order of sequence of the preferred AED training device training feature menu items 40, vertically includes the following choices:

1) Shock Scenarios or Preset/Preprogrammed Scenarios. Horizontally depicted within this menu item are a number of preset/preprogrammed scenario options, where each scenario is provided with a description of the AED training device preset shock sequence, e.g., there are 5 horizontal options depicted, such as Shock/No Shock/Shock, Shock/Shock/Shock, etc.
2) Shock Type. Horizontally depicted within the menu item are options of whether the shock is automatic or semi-automatic.
3) Ventilations. Horizontally depicted within this menu item are options of whether the need for requiring ventilations is on or off.
4) Metronome. Horizontally depicted within this menu item are options of whether the audio metronome to provide CPR timing indications to the student using the AED training device is on or off.

Using the first menu item 40, Shock Scenario, the AED training device training options 42 are selected from numerous preprogrammed listings audibly provided by the audio system 30, 70 to the AED trainer or teacher. The term "Shock" is used to indicate to a student that the AED training device is in condition to provide a simulated electrical therapy to a simulated patient, or a shock, which in an actual AED device would deliver electrical therapy to a patient. It is repeated for clarity that the AED training device of the present application is not capable of providing any electrical therapy or other diagnosis or treatment to a patient.

The present AED training device 10 includes a default setting, in the event no specific programming of the electronic device is desired. The default settings may include:
1) Shock Scenario—Shock/Shock/Shock
2) Semi-Automatic
3) Ventilations on
4) CPR Metronome on In the setup mode, the menu and change buttons 50, 60 as described here are enabled, as are additional AED training device dedicated function or instant access controls, such as a volume button 32, language button 34 and power button 14. It is understood that the dedicated function buttons indicated in the present embodiment, for example the language function control button 34, could be included as programmed features in the setup mode. In the present embodiment, English and Spanish languages are provided for selection by the user, as shown in FIG. 4. Additional inputs may also be provided by the manufacturer using a preprogrammed flash drive with the desired setup instructions via a standard USB port 36 interconnected with the control system 18 and memory 16.

The user or trainer using the AED training device 10 may enter the setup mode for programming the device with the desired training features from any device state by pressing the menu button 50. The change button 60 cannot be used to enter the setup mode, and is not enabled until after the user has entered the setup mode. The change button 60 is ignored in all other device states, including off.

Upon entering the training mode, the LED output indicators 19 and audio output system 30, 70 provided in the AED training device 10 will indicate that the device is in Shock condition, the option is provided so that the student may prepare to perform a simulation of the proper technique to be used for the condition being simulated. The AED training device 10 audio output control system 30, 70 is interconnected with the control system and memory 18, 16 and includes an electrically connected speaker 30 for replaying the preprogrammed voice instructions.

In the present embodiment, the number of the preprogrammed emergency scenario prompt is always the first training feature audible prompt delivered by the audio output control system 30, 70 when the setup mode is entered by the AED training device. The order of the programmed training options 42 heard is always repeated and played in the same order. This is true regardless of where in the menu item listing the device was when it last exited the setup mode. However, alternative training feature menu item order sequencing could be programmed.

The AED training device 10 will remain in setup mode until a setup timer, also provided as shown in FIG. 3, either times out or the user exits by pressing the power button 14, to turn the device off. The setup timer is preset, for example, to a 2 second time period that resets any time either control button 50, 60 is pressed. The timer is started after the corresponding audio prompt is delivered or played by the audio system 70.

By either pressing or selecting the power button 14 or doing nothing (and simply waiting for the setup timer to time out), the AED training device 10 exits the setup mode.

Upon exiting from the setup mode, the audio output control system 30, 70 sounds a single beep, the illuminated shock button 24 turns off, and the AED training device exits to power off mode, with all new programmed training option 42 selections saved to AED training device memory 16.

Navigation of the programming system 11 by the user using the menu and change buttons 50, 60 is further described as follows. Once the setup menu is entered, these menu and change hardware buttons on the AED training device are used to move within the programming system 11. The menu button 50 can be repeatedly pressed, selected or operated to scroll through the currently programmed training options 42. Each selection will generate a corresponding prompt via the audio system 30, 70, which provides an audio explanation of the training option 42 to the user. The first selection of the menu button 50 to enter the setup menu always voice prompts the currently selected training option 42 of the first menu item 40 prompt. In the current example, this is the current emergency scenario prompt. The second or next item played will always voice prompt the current second menu item 40, for example, shock type, and so on scrolling through the training options 42 currently selected within the menu item 40 by pressing the menu button 50. That is, each successive menu button 50 operation or selection will advance the audio output control system 70 to the next menu item and sound or voice the prompt to audibly play the currently programmed training feature option 42.

If the menu button 50 is pressed again before the previous voice prompt has been completed, that voice prompt will be interrupted and the next training option voice prompt will be played. In this way, the user can advance or scroll through the menu items quickly in order to reach the desired training option 42. Pressing the menu button 50 after hearing the last training option will return the control system 18 and the user back to the first training option 42 programmed in the menu item 40. Thus, the menu items are in a circular loop, and return to the first item after voice prompting the last item. Whenever the scenario menu item training option is voice prompted or played, a description of the Shock/No-Shock sequence will be played following a brief pause after the number of the scenario training option 42 programmed is played.

The change button 60 is only activated after the menu button 50 has been pressed at least one time. Thus, the change button 60 only works within the audio setup menu programming operation. Whenever the change button 60 is pressed, the electronic control system 18 plays the next option item, so that the name of the new option selected may be heard. For example, if "Shock Scenario 1" was just voice prompted or played, pressing the change button 60 will voice prompt to play "Shock Scenario 2." Another selection of the change button 60 will voice prompt to "Shock Scenario 3." The change menu button, accessing the training feature options 42, are also circular, in that any selection following the final available option 42 will return to the first option for that menu item 40 and will continue or repeat through the options 42. Training feature menu items 40 with only two options, such as "on" and "off" will appear to toggle back and forth between each option. As with the menu button 50, if the change button 60 is pressed before the previous voice prompt has been completed, the voice prompt will be interrupted and the next option voice prompt will be played, so the user can quickly advance to reach the desired option.

It should be understood that the user can alternate between the menu and change selections as desired, each time advancing to the next menu item 40 or training option 42. The most recent training option selections played are always saved to the AED training device memory 16 whenever the setup menu is exited.

As an example of use, if the user wanted to know the current settings for the AED training device without making any changes, they could simply press the menu button 50 repeatedly and listen to each currently selected training feature option 42 for each menu item 40 available in the list. The shock scenario will always be the first menu item played upon entry into the setup mode. Each press of the menu button 50 advances to the next feature in the menu item list, and circles back to the first item in the list, in an endless loop. At any point when listening to the currently selected menu options (by pressing the menu button repeatedly), if the user did not hear the desired training feature option item 42 for that menu item 40, they can change the option 42 by pressing the change button 60 until they hear the desired training option 42. The last option heard becomes the selected option that is saved to the AED training device memory 16 within the control system 18.

Certain embodiments of the invention have been described with specificity in order to improve understanding of the invention. However, many variations and modifications will become apparent to a person of ordinary skill in the art. For example, the present system provides for low cost programming of the electronic AED training device using only the two (2) tactile switches with plastic caps or covers, provided as the change and menu buttons 50, 60, and the audio prompts, which are stored in the existing device memory 16 and played by the existing device speaker 30. As liquid crystal displays (LCD) and thin film transistor (TFT) displays are expensive, the elimination of these types of visual display components, reduces cost, as well as makes more space available on the visual surface of AED training device. Since such displays are not required during use of the AED training device by a student during training, it is advantageous to eliminate visual displays from the surface of the AED training device. Still further programming is easy to expand to include as many additional features and options as desired, without the addition of further hardware components, simply by using the additional vertical and horizontal programming capabilities in the available software of the matrix setup. It is therefore expected and intended that the certain changes and modifications may be practiced which will still fall within the scope of the appended claims.

We claim:

1. An electronic automated external defibrillator training device having:
    a controller configured to execute instructions to perform a training simulation and provide a programming interface for configuring a set of menu items for the training simulation, wherein the training simulation comprises a simulated electrical therapy to a simulated patient;
    a set of training pads in electronic communication with the controller and usable by the controller to perform the training simulation;
    a memory configured to store a set of alternative training feature options and a set of programmed training feature options, wherein;
        the set of alternative training feature options comprises, for each of the set of menu items, two or more alternative training feature options for that menu item; and
        the set of programmed training feature options comprises, for each of the set of menu items, an indication of a currently programmed training feature option for that menu item, wherein the currently programmed training feature option is one of the two or more alternative training feature options for that menu item;
    a speaker configured to provide audio output indicators based upon signals from the controller, the audio output indicators comprising audible voice prompts that describe the set of alternative training feature options; and
    a set of manual input controls comprising two manual buttons in electronic communication with the controller, wherein:
        a first manual button, usable to advance through the set of menu items of the audio menu, operates to provide signals to the controller to select by advancing through and audibly playing by a single actuation of the first manual button, via the speaker, audible voice prompts for a next programmed training feature option of the set of programmed training feature options for the training simulation performed by the electronic automated external defibrillator training device, and
        a second manual button, usable to change the currently programmed training feature option for the set of menu items, operates to provide signals to the controller to change the indication of the currently programmed training feature option of the set of programmed training feature options for which an audible voice prompt was most recently played to indicate one of the corresponding two or more alternative training feature options, which change is saved to the memory for use by the electronic automated external defibrillator training device when performing the training simulation.

2. The electronic automated external defibrillator training device of claim 1, wherein the two manual buttons are tactile switches.

3. The electronic automated external defibrillator training device of claim 1, wherein the second manual button is operable only following a first activation of the first manual button.

4. The electronic automated external defibrillator training device of claim 1, wherein the programming interface further comprises a timer for deactivating the programming interface after passage of a predetermined desired amount of time following activation of either the first or second manual buttons.

5. The electronic automated external defibrillator training device of claim 1, wherein the audible voice prompts comprise audible voice prompts in a first playback language and audible voice prompts in a second playback language; and
    wherein the set of manual input controls further comprises a third manual input control in electronic communication with the controller, the third manual input control configured to select between the first playback language and the second playback language upon activation.

6. The electronic automated external defibrillator training device of claim 5, further comprising a USB port in electronic communication with the controller, wherein the controller is configured to receive one or more of audible voice prompts in other languages and additional training options via the USB port.

* * * * *